United States Patent
Suh et al.

(10) Patent No.: US 11,167,091 B2
(45) Date of Patent: Nov. 9, 2021

(54) PRECISION SYRINGE

(71) Applicant: The Board of Regents of the University of Nebraska, Lincoln, NE (US)

(72) Inventors: Donny Suh, Omaha, NE (US); Ronald Linke, Elk Horn, NE (US); Tyler Scherr, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 173 days.

(21) Appl. No.: 16/484,171

(22) PCT Filed: Feb. 15, 2018

(86) PCT No.: PCT/US2018/018383
§ 371 (c)(1),
(2) Date: Aug. 7, 2019

(87) PCT Pub. No.: WO2018/152335
PCT Pub. Date: Aug. 23, 2018

(65) Prior Publication Data
US 2020/0368443 A1   Nov. 26, 2020

Related U.S. Application Data

(60) Provisional application No. 62/459,143, filed on Feb. 15, 2017.

(51) Int. Cl.
*A61M 5/315* (2006.01)

(52) U.S. Cl.
CPC . *A61M 5/31513* (2013.01); *A61M 2205/6063* (2013.01)

(58) Field of Classification Search
CPC ........... A61M 5/31513; A61M 5/31511; A61B 5/150259
See application file for complete search history.

(56) References Cited

U.S. PATENT DOCUMENTS 3,325,061 A * 6/1967 Ellsworth ........... A61M 5/3137
                                                           222/386
3,749,284 A * 7/1973 Kloehn ............. A61M 5/31591
                                                           222/43

(Continued)

FOREIGN PATENT DOCUMENTS

| KR | 970001377 A | 1/1997 |
| KR | 20120015829 A | 2/2012 |
| KR | 101143929 B1 | 5/2012 |

OTHER PUBLICATIONS

International Search Report dated May 28, 2018 for PCT/US2018/018383.

*Primary Examiner* — Bradley J Osinski
(74) *Attorney, Agent, or Firm* — Nasr Patent Law LLC; Faisal K. Abou-Nasr

(57) ABSTRACT

A precision syringe includes a syringe barrel and plunger that has a base, an internal portion, and an external portion. The internal portion of the plunger extends longitudinally into the syringe barrel. The internal portion has a first end coupled to the base and a second end that is configured to push fluid out of and/or suction fluid into the syringe barrel. The external portion extends longitudinally along an outer surface of the syringe barrel. The external portion has a first end coupled to the base and a second end that is configured to receive an applied force that causes the plunger to move relative to the syringe barrel so that the second end of the internal portion is actuated through a portion of the syringe barrel (e.g., to dispense fluid from or suction fluid into the syringe barrel).

16 Claims, 11 Drawing Sheets

(56) References Cited

U.S. PATENT DOCUMENTS

| | | |
|---|---|---|
| 5,115,816 A | 5/1992 | Lee |
| 6,368,308 B1 * | 4/2002 | Nerney .............. A61M 5/31511 |
| | | 604/208 |
| 7,118,556 B2 * | 10/2006 | Nerney ............... A61M 5/3148 |
| | | 604/227 |
| 9,186,463 B2 | 11/2015 | Hoyle, Jr. |
| 2012/0059347 A1 * | 3/2012 | Freed .................. A61M 5/3129 |
| | | 604/500 |

\* cited by examiner

PRECISION SYRINGE

CROSS-REFERENCE TO RELATED APPLICATIONS

The present application claims the benefit under 35 U.S.C. § 119(e) of U.S. Provisional Application Ser. No. 62/459,143, filed Feb. 15, 2017, and titled "Suh Precision Injection Syringe," which is herein incorporated by reference in its entirety.

BACKGROUND

Syringes are often used to dispense or collect fluids. For example, syringes may be used to dispense and/or inject medications, to collect biological fluid samples, and so forth. It is often necessary to position a syringe at a specific location and/or in a specific orientation while dispensing or collecting fluid. In some situations, properly positioning the syringe can make it difficult for a user to dispense or collect fluid with the syringe in an accurate and precise manner.

SUMMARY

A precision syringe is disclosed with a plunger that can be actuated (e.g., by pushing or pulling upon an external portion of the plunger) from a first end near a base of the syringe and also from a second end near a tip of the syringe. The precision syringe includes a syringe barrel and plunger that has a base, an internal portion, and an external portion. The internal portion of the plunger extends longitudinally into the syringe barrel. The internal portion has a first end coupled to the base and a second end that is configured to push fluid out of and/or suction fluid into the syringe barrel. The external portion extends longitudinally along an outer surface of the syringe barrel. The external portion has a first end coupled to the base and a second end that is configured to receive an applied force (e.g., a push or pull) that causes the plunger to move relative to the syringe barrel so that the second end of the internal portion is actuated through a portion of the syringe barrel (e.g., to dispense fluid from or suction fluid into the syringe barrel). In some embodiments, the external portion has a projection disposed at the second end, where the projection is configured to receive the applied force (or at least a portion of the applied force). For example, the projection can make it easier to push or pull the second end of the external portion of the plunger so that the plunger moves relative to the syringe barrel.

In some embodiments, the precision syringe further includes a guide disposed upon the outer surface of the syringe barrel. The external portion can include an indentation that fits over at least a portion of the guide so that the external portion slides along the guide in a longitudinal direction relative to the syringe barrel. For example, the guide may have a shape that is cooperative with a shape of the indentation formed within the external portion of the plunger so that one or more inner surfaces of the indentation are in contact with one or more surfaces of the guide. The guide may be configured to at least partially constrain a movement of the plunger relative to the syringe barrel. For example, the guide may be configured to at least partially prevent the external portion of the plunger from moving perpendicular to a longitudinal axis of the syringe barrel.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Overview

Syringes are often employed in delicate procedures where it may be necessary to position or orient a syringe in a manner that makes it difficult to apply a force to (e.g., push or pull upon) the syringe's plunger in order to dispense or collect fluid. To provide a user with ability to actuate a syringe plunger from a position at or near the front end (e.g., tip) or rear end (e.g., base) of the syringe, a precision syringe is disclosed with a plunger that can be actuated from a rear end (e.g., base) of the plunger or by alternatively applying force to an end of the external portion of the plunger that is near the tip (e.g., dispensing/collecting end) of the syringe. Consequently, the syringe can be placed in a variety of positions and orientations without making it difficult for the plunger to be actuated. For example, the tip of the syringe can be held near a target location while the plunger is actuated to dispense or collect fluid by pushing or pulling the end of the external portion of the plunger that is near the tip.

Example Implementations

Figure 1:
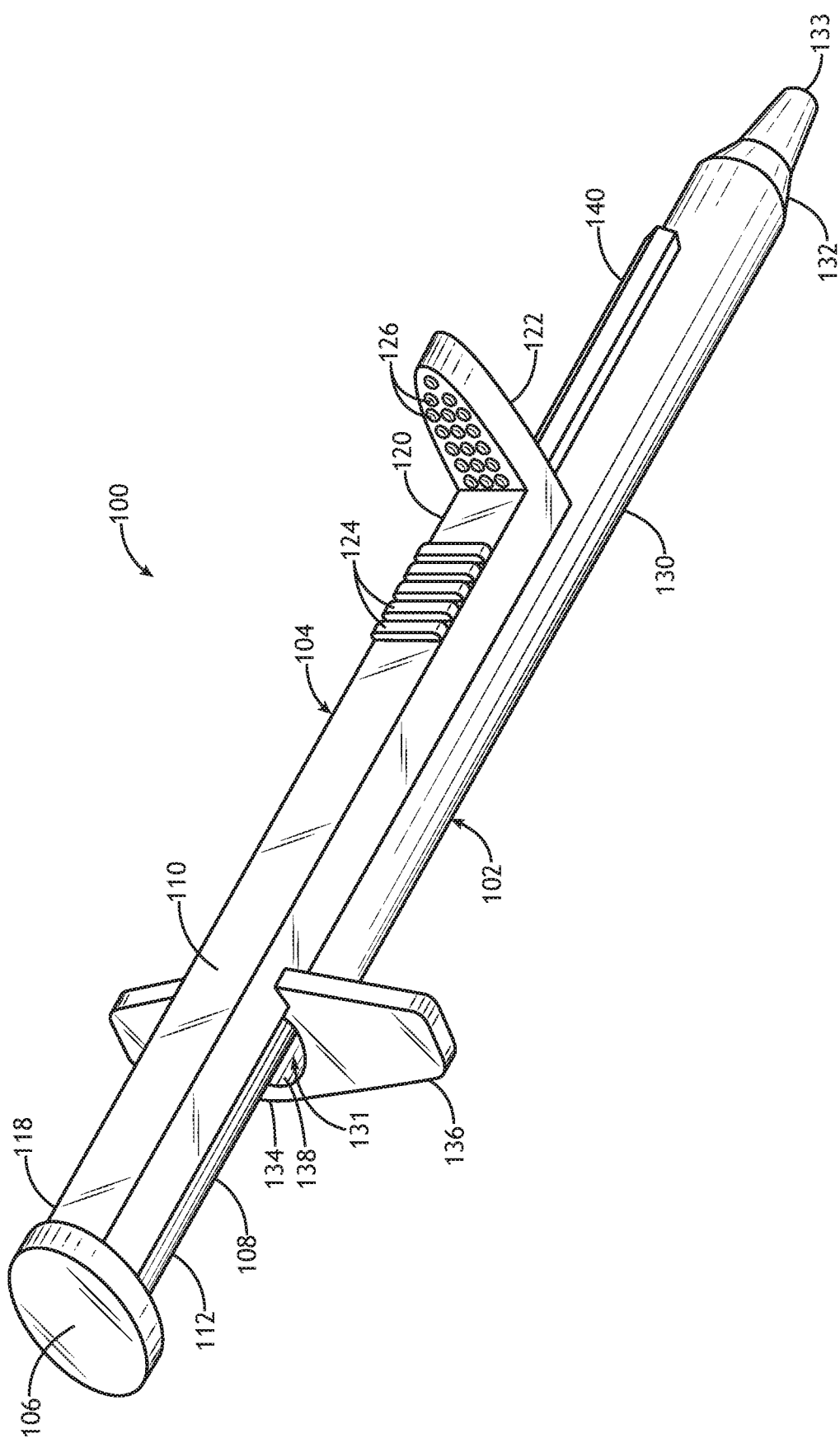
FIG. 1 is a perspective view of a precision syringe, in accordance with an example embodiment of the present disclosure.
Figure 2:
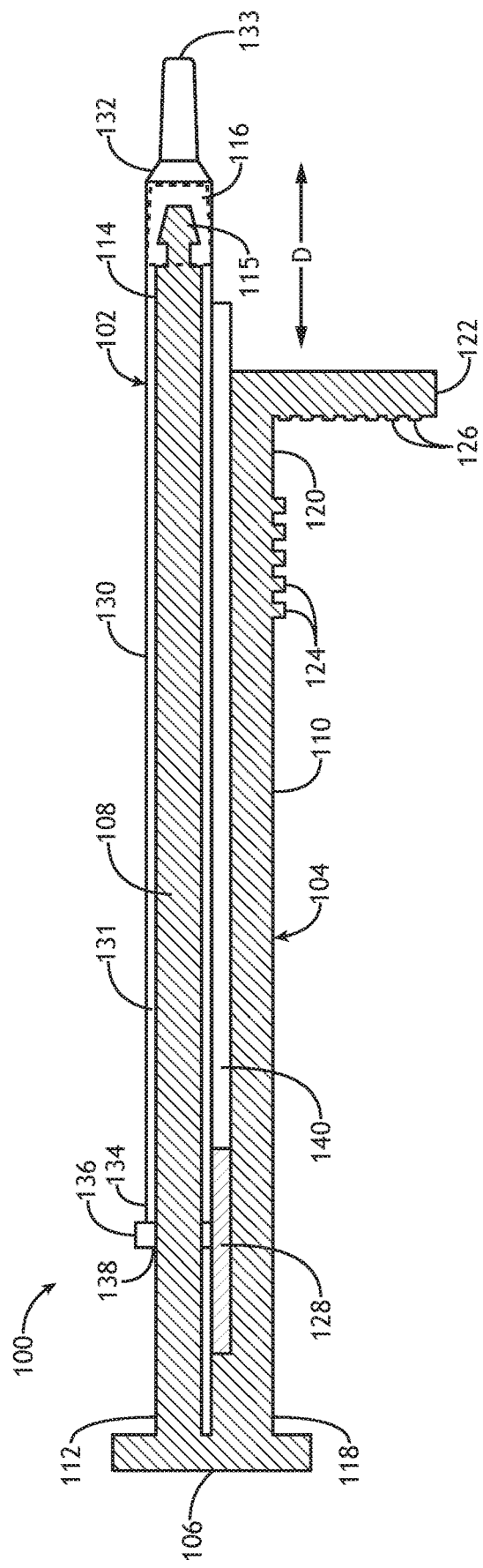
FIG. 2 is a cross-sectional side view of a precision syringe, such as the precision syringe illustrated in FIG. 1, in accordance with an example embodiment of the present disclosure.
Figure 3:
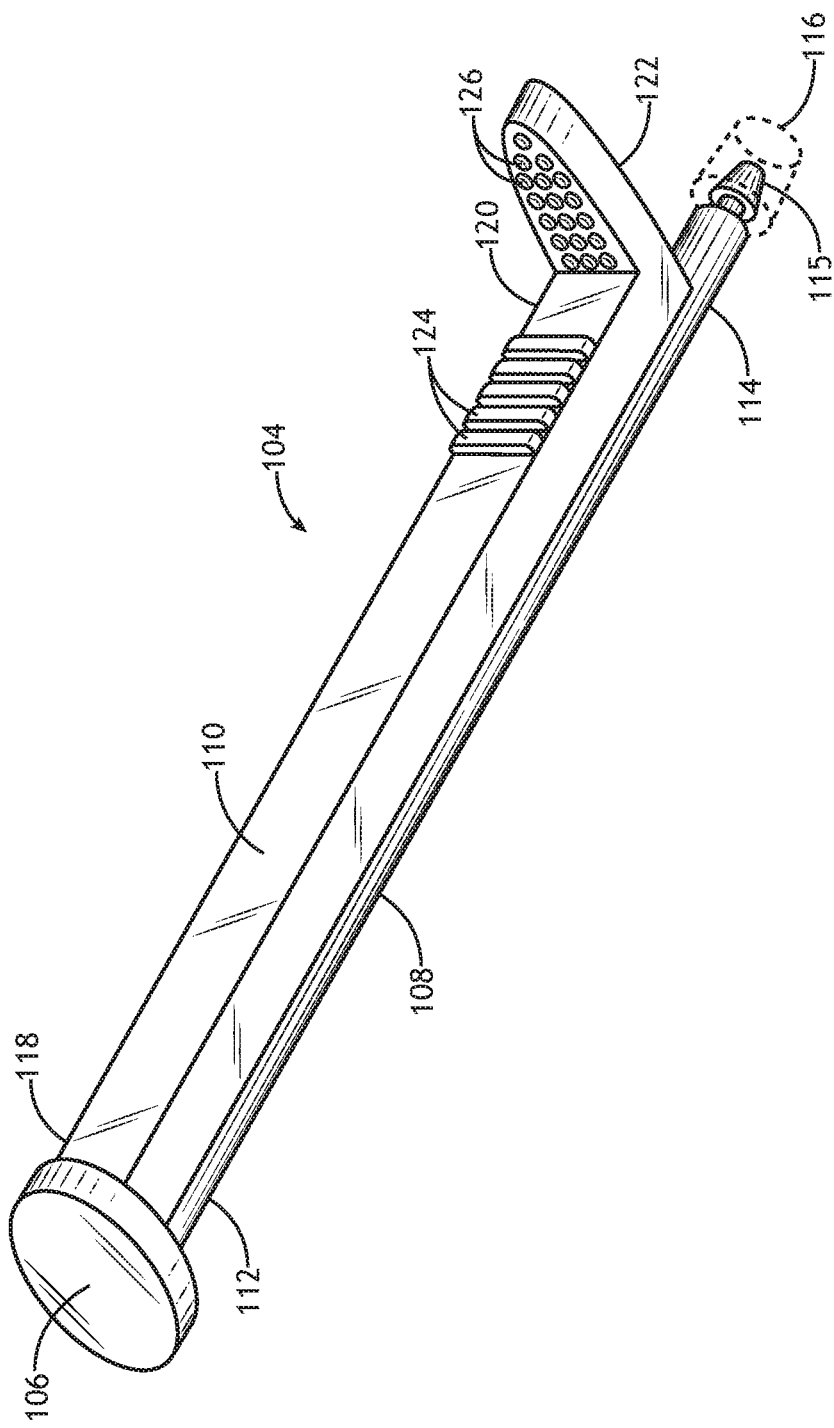
FIG. 3 is a top perspective view of a syringe plunger for a precision syringe, such as the precision syringe illustrated in FIG. 1, in accordance with an example embodiment of the present disclosure.

FIGS. 1 and 2 show a precision syringe 100 in accordance with embodiments of the present disclosure. The syringe 100 includes a syringe barrel 102 and a plunger 104 that is configured to be partially disposed within the syringe barrel 102. The syringe barrel 102 includes a body 130 (e.g., a tubular body) that defines a cavity 131 configured to contain fluid (e.g., liquid or gas). Examples of fluids that can be collected and/or dispensed by the syringe 100 include, but are not limited to, sample fluids (e.g., biological or other fluid samples), solutions including medications, therapeutic agents, contrast agents, etc., antibiotic/antiseptic solutions, and the like.

Figure 11:
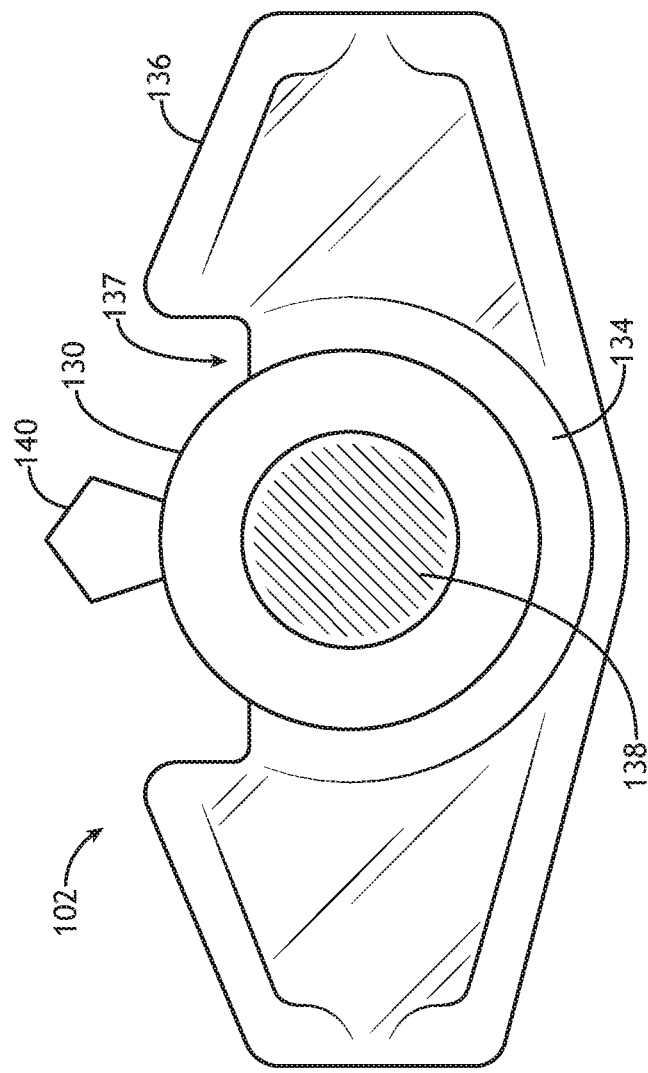
FIG. 11 is a rear end view of a syringe barrel for a precision syringe, such as the precision syringe illustrated in FIG. 1, in accordance with an example embodiment of the present disclosure.

The syringe barrel 102 has a first end 134 with an opening 138 that leads into the interior cavity 131 defined by the body 130. The opening 138 is configured to receive an internal portion 108 of the plunger 104. For example, the internal portion 108 of the plunger 104 is configured to extend longitudinally into the syringe barrel 102 (i.e., into the cavity 131 defined by the body 130) when the plunger 104 is actuated towards a second end 132 of the syringe barrel 102. As shown in FIG. 11, the syringe barrel 102 can also have a flange 136 formed around the opening 138. The flange 136 may include a notch 137 that surrounds at least a portion (e.g., at least partially surrounds an external portion 110) of the plunger 104 when the internal portion 108 of the plunger 104 is at least partially inserted into the syringe barrel 102. The notch 137 may be opposite a surface of the syringe barrel 102 having indicator lines (e.g., volumetric numbering lines) that are formed and/or printed along the body 130 of the syringe barrel 102.

In embodiments, the second end 132 of the syringe barrel 102 has a tip 133 formed at the second end 132 for dispensing and/or collecting fluid. The tip 133 may be tapered or cylindrical. In some embodiments, the tip 133 can include or can be coupled to a needle that is used to penetrate a membrane (e.g., skin) to inject or collect fluid through the membrane. In other embodiments, the tip 133 can be coupled to a tube or nozzle to dispense fluid through the tube or with greater precision or at higher pressure using the nozzle.

In some embodiments, the syringe barrel 102 is at least partially patterned with raised ridges around the circumference of the body 130 except for a portion having indicator lines (e.g., volumetric numbering lines) that are formed and/or printed along the body 130 of the syringe barrel 102. For example, the raised edges may run from the tip 133 to a distance of approximately 10 to 30 mm (e.g., 20 mm) along the outer surface of the syringe barrel 102.

The plunger 104 is shown partially inserted into the syringe barrel in FIGS. 1 and 2. Detailed views of the plunger 104 are also shown FIG. 3 through 9. The plunger 104 includes a base 106 coupled to the internal portion 108 of the plunger 104 and also to the external portion 110 of the plunger 104. The internal portion 108 of the plunger 104 extends longitudinally into the syringe barrel 102 and has a first end 112 coupled to the base 106. The internal portion also has a second end 114 opposite the first end 112. The second end 114 is configured to push fluid out of and/or suction fluid into the syringe barrel 102. In some embodiments, the second end 114 flares out to contact or nearly contact an inner surface of the body 130 of the syringe barrel 102 so that the second end 114 can push fluid out of or suction fluid into the syringe barrel 102 (e.g., into or out of the interior cavity 131 defined by the body 130) when the second end 114 is actuated through a portion of the syringe barrel 102. In some embodiments, the internal portion 108 of the plunger 104 has a pusher 116 disposed at the second end 114 for pushing fluid out of or suctioning fluid into the syringe barrel 102. For example, the pusher 116 can be a plug (e.g., rubber plug, plastic plug, metal plug, ceramic plug, or the like) disposed at the second end 114 of the internal portion 108 of the plunger 104. In some embodiments, the pusher 116 is coupled to the second end 114 of the plunger 104. For example, the pusher 116 may be coupled to the second end 114 by an adhesive or by a form-fitting tip 115 that can be forced into the pusher 116 (e.g., as shown in FIG. 2). In other embodiments, the pusher 116 is a flared portion of the second end 114. For example, the pusher 116 may be made from the same material as the internal portion 108 of the plunger 104 and/or part of the same print or mold.

The external portion 110 of the plunger 104 extends longitudinally along an outer surface of the syringe barrel 102 and also has a first end 118 coupled to the base 106. The base 106 can be configured to support the internal portion 108 of the plunger 104 parallel (or substantially parallel) to the external portion 110 of the plunger 104. For example, the internal portion 108 and external portion 110 of the plunger 104 can be coupled to a surface of the base 106 that is perpendicular (or substantially perpendicular) to a longitudinal axis 141 (shown in FIG. 10) of the syringe barrel 102, where each of the internal portion 108 and external portion 110 of the plunger 104 extend along or parallel to the longitudinal axis 141. In an embodiment shown in FIG. 7, an angle $\theta_1$ between the internal portion 108 and the base 106 is in the range of 80 to 100 degrees (e.g., $\theta_1$ can be a 90 degree angle or nearly 90 degree angle), and an angle $\theta_2$ between the external portion 110 and the base 106 is also in the range of 80 to 100 degrees (e.g., $\theta_2$ can be a 90 degree angle or nearly 90 degree angle).

In some embodiments, the external portion 110 of the syringe plunger 104 is connected to the base 106 at a connection site that is approximately 1 to 3 mm from the center of the base 106 (e.g., 1.67 mm out from the center of the base 106). The external portion 110 may extend parallel to the longitudinal axis 141 of the syringe barrel 102 to a distance of approximately 10 to 25 mm (e.g., 15 mm) when the internal portion 108 of the plunger 104 is fully inserted into the syringe barrel 102. The external portion 110 may have a width no greater than a width of the syringe barrel 102 (e.g., the width or diameter of the body 130) and a depth of approximately 1 to 5 mm (e.g., 3 mm).

The plunger 104 can be actuated when force is applied to the base 106. For example, the plunger 104 can move relative to the syringe barrel 102 when the base 106 is pressed, pushed, pulled, or otherwise actuated. The plunger 104 can also be actuated when force is applied to the external portion 110 of the plunger 104. For example, the external portion 110 has the first end 118 coupled to the base 106 and a second end 120 that is configured to receive an applied force (e.g., a push or pull) that causes the plunger 104 to move relative to the syringe barrel 102 so that the pusher 116 is actuated through a portion of the syringe barrel 102 (e.g., through the interior cavity 131 defined by the body 130 to dispense fluid from or suction fluid into the interior cavity 131).

Figure 7:
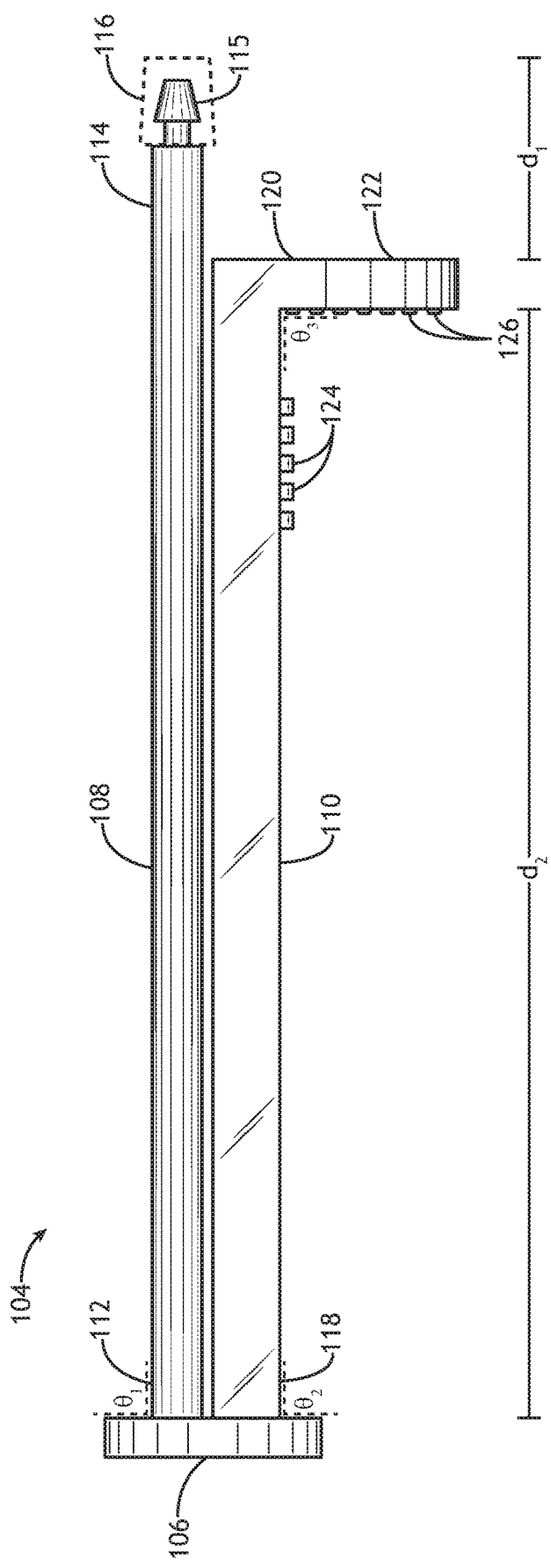
FIG. 7 is a side view of a syringe plunger for a precision syringe, such as the precision syringe illustrated in FIG. 1, in accordance with an example embodiment of the present disclosure.
Figure 8:
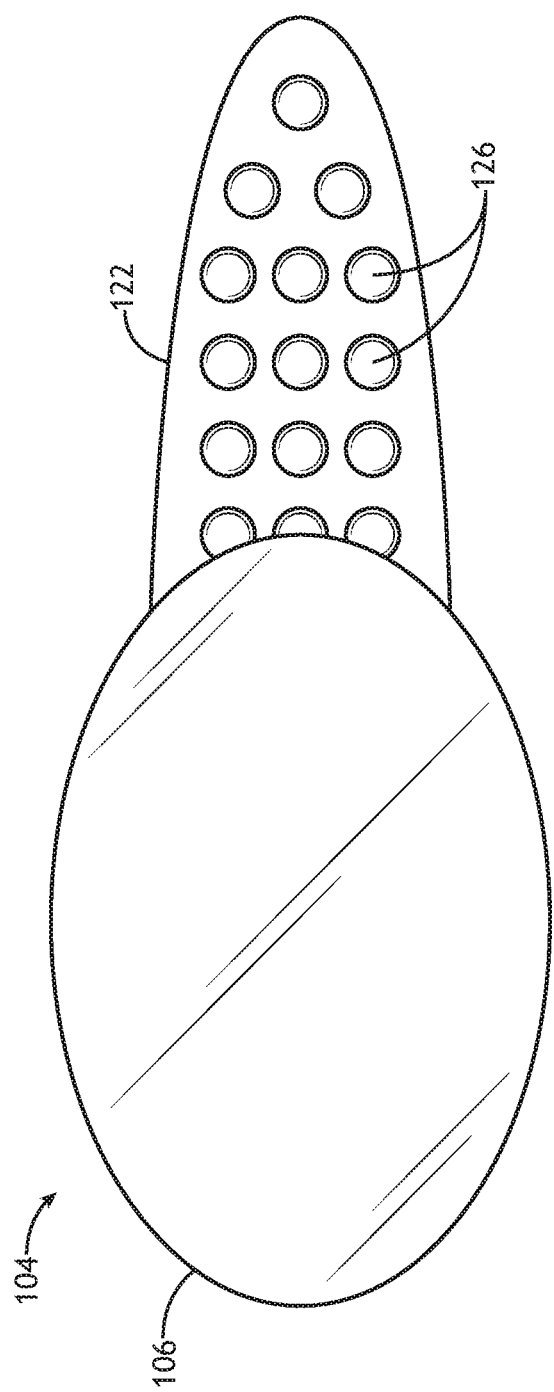
FIG. 8 is a rear end view of a syringe plunger for a precision syringe, such as the precision syringe illustrated in FIG. 1, in accordance with an example embodiment of the present disclosure.

In some embodiments, the external portion 110 of the plunger 104 has a projection 122 disposed at the second end 120 of the external portion 110. The projection 122 can be configured to receive the applied force (or at least a portion of the applied force). For example, the projection 122 can make it easier to push or pull the second end 120 of the external portion 110 of the plunger 104 so that the plunger 104 moves relative to the syringe barrel 102. In some embodiments, the projection 122 is perpendicular (or substantially perpendicular) to the longitudinal axis 141 of the syringe barrel 102. For example, as shown in FIG. 7, the projection 122 can extend from the external portion 110 of the plunger 104 at an angle $\theta_3$ in the range of 80 to 100 degrees (e.g., at a 90 degree angle or nearly 90 degree angle). In embodiments where the projection 122 is perpendicular (or substantially perpendicular) to the longitudinal axis 141 of the syringe barrel 102, the projection 122 may be configured to indicate an amount of collected or dispensed fluid. For example, the projection 122 can be aligned with indicator lines (e.g., volumetric numbering lines) that are formed and/or printed along the body 130 of the syringe barrel 102.

In some embodiments, a distance $d_1$ between the pusher 116 and the projection 122 is less than a distance $d_2$ between the base 106 and the projection 122. In this regard, the projection 122 can be nearer to the tip 133 of the syringe barrel 102 than it is to the base 136 of the syringe barrel 102 when the plunger 104 is actuated to dispense or collect fluid via the tip 133. In some embodiments, the projection 122 can have, but is not limited to, a teardrop shape that protrudes away from the syringe barrel 102 a distance of approximately 5 to 15 mm (e.g., 11.5 mm) and may also have a width no greater than a width of the syringe barrel 102 (e.g., the width or diameter of the body 130) and a depth of approximately 1 to 5 mm (e.g., 3 mm).

In some embodiments, an entirety of the plunger 104 (e.g., the base 106, the internal portion 108, and the external portion 110) may be a common structure. In this regard, an entirety of the plunger 104 may move relative to the syringe barrel 102 when any portion of the plunger 104 is actuated relative to the syringe barrel 102. For example, the plunger 104 can move relative to the syringe barrel 102 when the base 106 is pressed, pushed, pulled, or otherwise actuated, and similarly when the second end 120 and/or projection 122 is pressed, pushed, pulled, or otherwise actuated. In some embodiments, the base 106, the internal portion 108, and the external portion 110 of the plunger 104 are all formed from a common mold or print. For example, the plunger 104 can be a common plastic, metal, or ceramic mold or print. In embodiments, the plunger 104 is formed from one or more biocompatible materials (e.g., biocompatible plastic, metal, and/or ceramic material).

In some embodiments, the external portion 110 of the plunger 104 includes surface texturing 126 on a surface of the projection 122 and/or surface texturing 124 on a surface of the external portion 110 that is adjacent to the projection 122. This can make it easier to push or pull the second end 120 of the external portion 110 of the plunger 104 so that the plunger 104 moves relative to the syringe barrel 102. For example, the surface texturing 124 and/or 126 on the external portion 110 of the plunger 104 and/or the projection 122 can provide an easier to grip surface that can be pushed or pulled with a finger more easily than a smooth surface. In some embodiments, the surface texturing 124 and/or 126 includes at least one indentation, protuberances, pattern of indentations, and/or pattern of protuberances on a surface of the external portion 110 of the plunger 104 and/or projection 122. For example, FIG. 1 shows surface texturing 124 including a line pattern of protuberances and surface texturing 126 including a dot pattern of protuberances. In some embodiments, the indentations or protuberances have a depth/height of approximately 0.2 to 1.5 mm (e.g., 0.5 mm) from the surface of the external portion 110 of the plunger 104 and/or the projection 122 on which the indentations or protuberances are formed.

Figure 4:
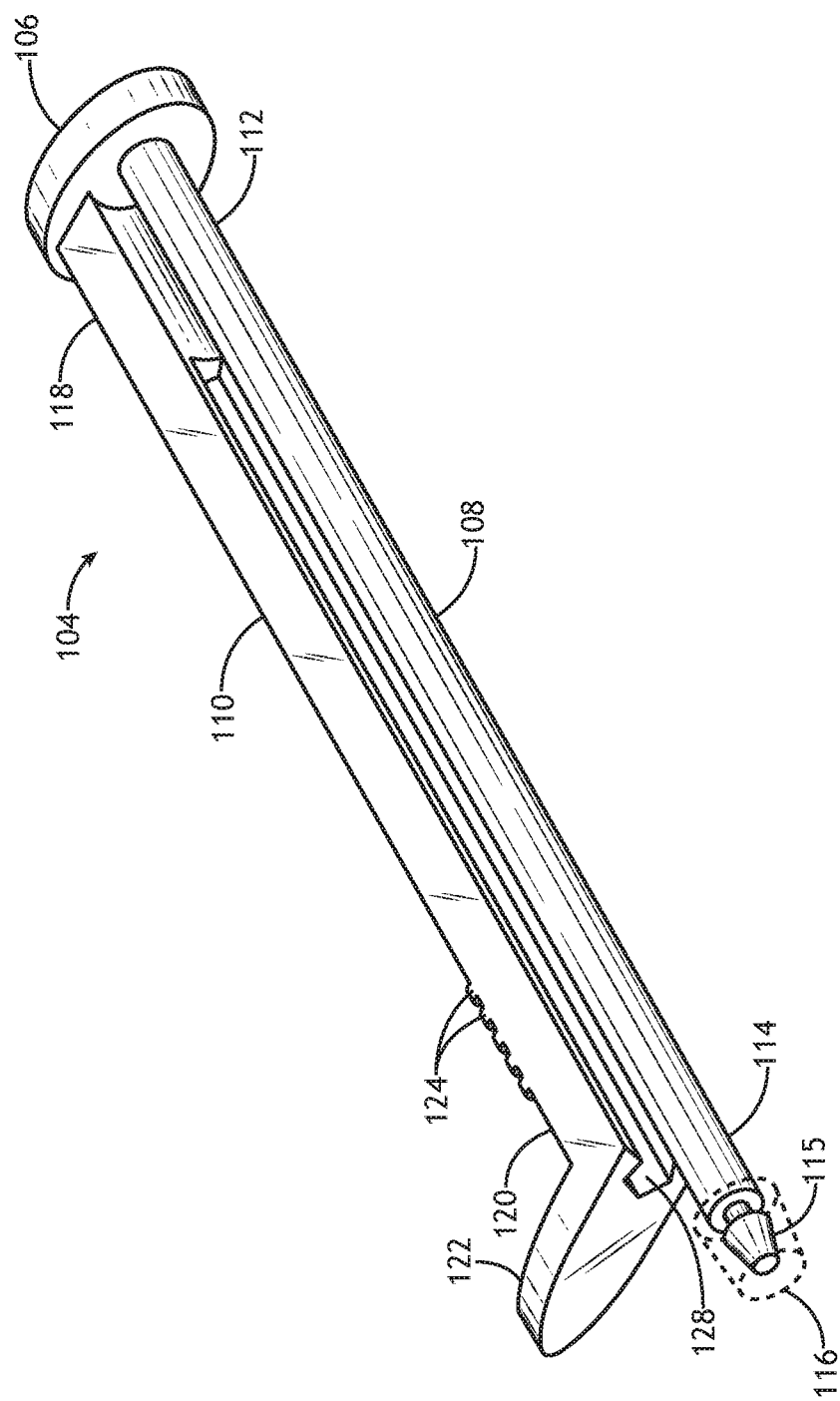
FIG. 4 is a bottom perspective view of a syringe plunger for a precision syringe, such as the precision syringe illustrated in FIG. 1, in accordance with an example embodiment of the present disclosure.
Figure 5:
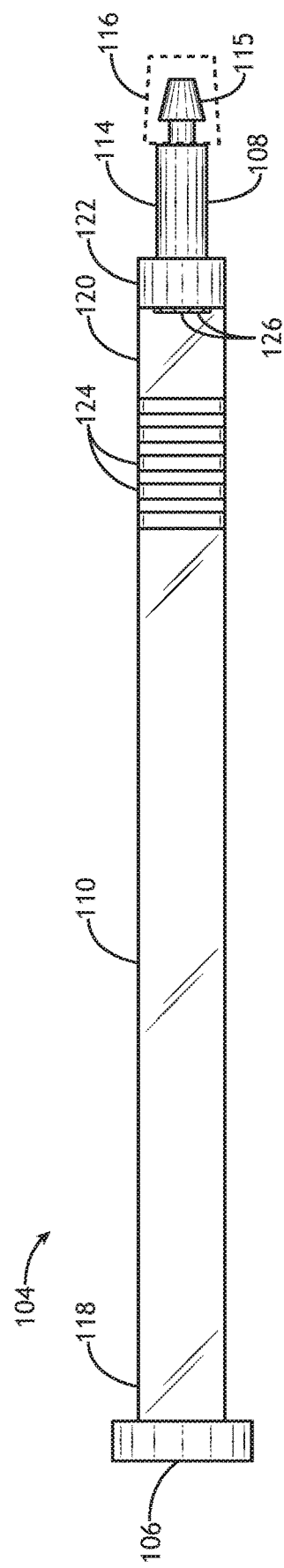
FIG. 5 is a top view of a syringe plunger for a precision syringe, such as the precision syringe illustrated in FIG. 1, in accordance with an example embodiment of the present disclosure.
Figure 6:
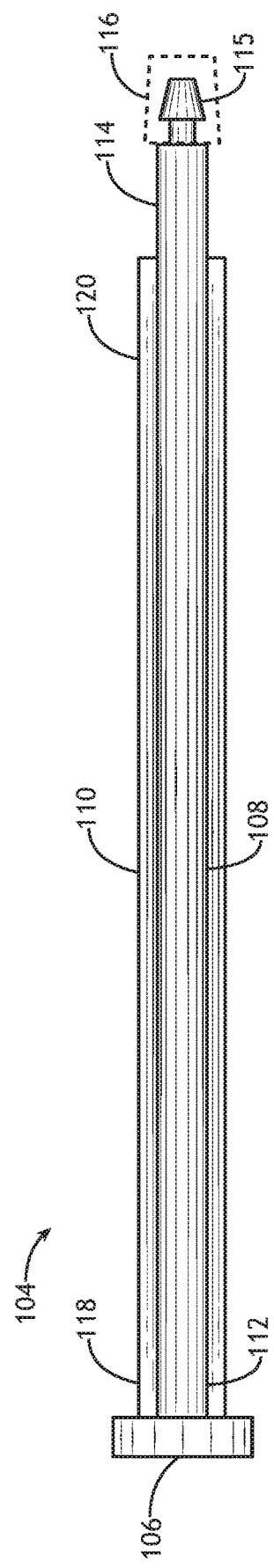
FIG. 6 is a bottom view of a syringe plunger for a precision syringe, such as the precision syringe illustrated in FIG. 1, in accordance with an example embodiment of the present disclosure.
Figure 9:
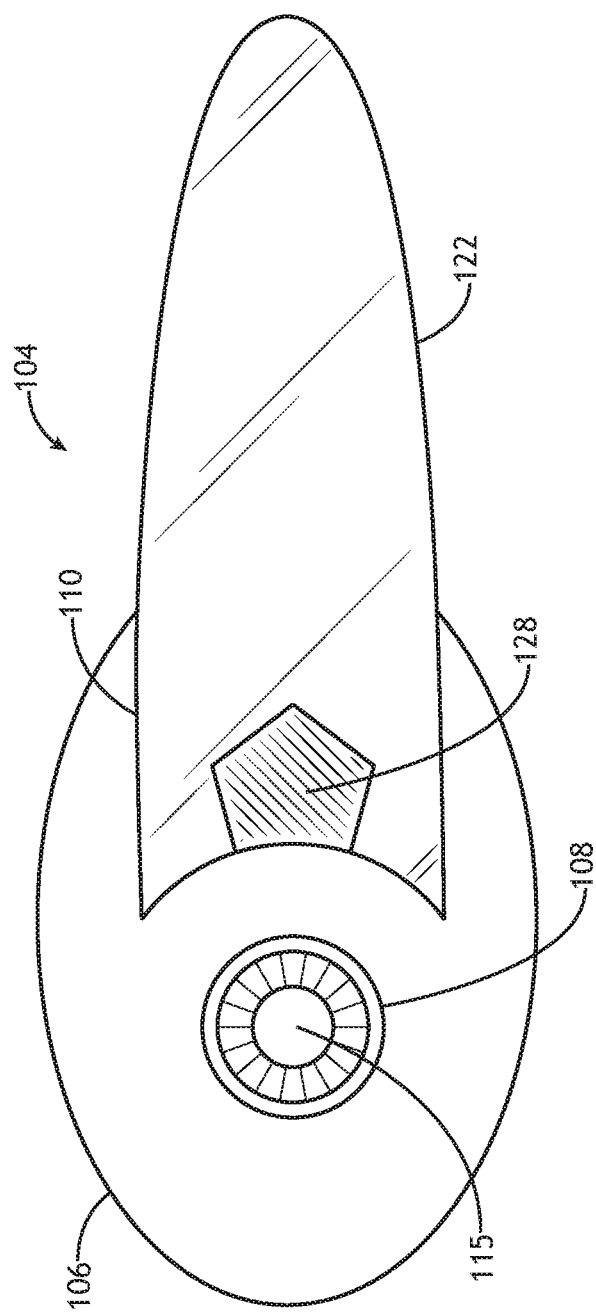
FIG. 9 is a front end view of a syringe plunger for a precision syringe, such as the precision syringe illustrated in FIG. 1, in accordance with an example embodiment of the present disclosure.

As shown in FIGS. 4 and 9, the external portion 110 of the plunger 104 can also include an indentation 128 that extends longitudinally through at least part of the external portion 110. Referring again to FIGS. 1 and 2, the indentation 128 can be configured to fit over at least a portion of a guide 140 on the syringe barrel 102 so that the external portion 110 of the plunger 104 slides along the guide 140 in a longitudinal direction D relative to the syringe barrel 102 when the plunger 104 is actuated (e.g., by pressing, pushing, or pulling upon the base 106, second end 120, and/or projection 122).

Figure 10:
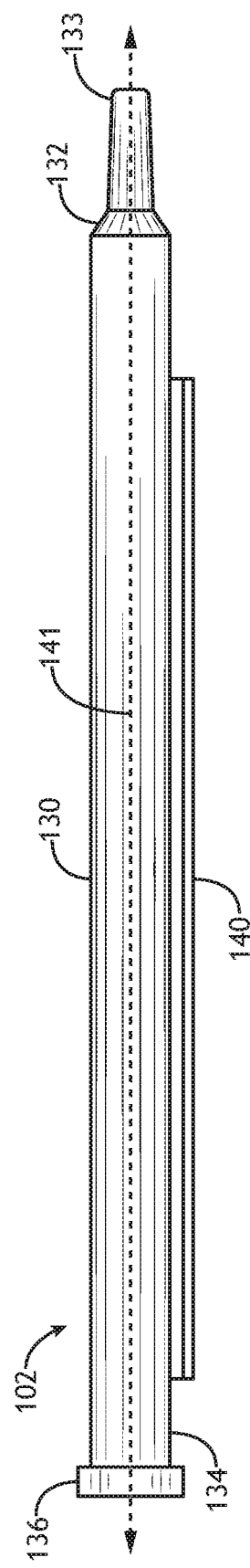
FIG. 10 is a side view of a syringe barrel for a precision syringe, such as the precision syringe illustrated in FIG. 1, in accordance with an example embodiment of the present disclosure.

FIGS. 10 and 11 show side and end views, respectively, of the syringe barrel 102 with the guide 140 extending longitudinally along the outer surface of the syringe barrel 102 (e.g., along at least a portion of the body 130). In embodiments, the guide 140 is opposite a surface of the syringe barrel 102 having indicator lines (e.g., volumetric numbering lines) that are formed and/or printed along the body 130 of the syringe barrel 102. As can be seen in FIGS. 9 and 11, the guide 140 may have a shape that is cooperative with a shape of the indentation 128 formed within the external portion 110 of the plunger 104 so that one or more inner surfaces of the indentation 128 are in contact with one or more surfaces of the guide 140 when the plunger 104 (i.e., the internal portion 108 of the plunger 104) is at least partially inserted within the syringe barrel 102. The guide 140 can have any shape that is cooperative with the shape of the indentation 128. For example, FIGS. 9 and 11 show the guide 140 and the indentation 128 having pentagonal cross-sections, where the guide 140 has a pentagonal cross-section with one side being curved in accordance with a curvature of the syringe barrel 102 (e.g., curving around at least a portion of the body 130). The guide 140 and the indentation 128 can have any cross-sectional shape, for example, triangular cross-sections, square cross-sections, circular cross-sections, or the like. In any configuration, the guide 140 may have one side or edge that is curved or otherwise shaped so that it forms a continuous (or substantially continuous) interface with the body 130 of the syringe barrel 102.

The guide 140 may be configured to at least partially constrain a movement of the plunger 104 relative to the syringe barrel 102. For example, the guide 140 may be configured to at least partially prevent the external portion 110 of the plunger from moving perpendicular to a longitudinal axis 141 of the syringe barrel 102 (e.g., from moving in any direction other than a longitudinal direction D along the outer surface of the syringe barrel 102). This provides stability for the user when the plunger 104 is being actuated and can help prevent inaccurate dosage or accidental repositioning of the syringe 100.

In an example use scenario, the syringe 100 can be held so that a second end 132 of the syringe barrel 102 is supported between a user's thumb and middle finger. The plunger 104 can then be actuated by applying force to the second end 120 of the external portion 110 of the plunger 104 and/or to the projection 122. This allows the user to actuate the plunger 104 with the user's index finger while maintaining the syringe 100 in a selected position and/or orientation with the user's thumb and middle finger. The user is not required to use another hand or readjust his/her grip of the syringe 100.

Conclusion

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore any dimensions, degrees, and/or numerical ranges provided herein are to be understood as non-limiting examples unless otherwise specified in the claims.

What is claimed is:

1. A syringe, comprising:
    a syringe barrel; and
    a plunger, the plunger having a base, an internal portion, and an external portion,
    the internal portion having a first end coupled to the base, the internal portion extending longitudinally into the syringe barrel and having a second end configured to push a fluid out of the syringe barrel,
    the external portion having a first end coupled to the base, the external portion extending longitudinally along an outer surface of the syringe barrel and having a projection disposed at a second end of the external portion, the projection configured to receive an applied force that causes an entirety of the plunger to move relative to the syringe barrel so that the second end of the internal portion is actuated through a portion of the syringe barrel, wherein a distance between the second end of the internal portion and the projection is less than a distance between the base and the projection, wherein the projection is perpendicular to the external portion of the plunger, wherein the projection extends a distance of 5 to 15 mm from the external portion of the plunger, wherein the projection includes surface texturing comprising a pattern of protuberances on the projection, and wherein the external portion of the plunger includes additional surface texturing on a surface of the external portion that is adjacent to the projection.

2. The syringe as recited in claim 1, wherein the internal portion and the external portion are perpendicular to the base and parallel to one another.

3. The syringe as recited in claim 1, wherein the projection is perpendicular to a longitudinal axis of the syringe barrel.

4. The syringe as recited in claim 1, wherein the plunger is formed from a common mold or print.

5. The syringe as recited in claim 1, further comprising:
    a guide disposed upon the outer surface of the syringe barrel, the guide configured to at least partially constrain a movement of the plunger relative to the syringe barrel.

6. The syringe as recited in claim 5, wherein the guide is configured to at least partially prevent the external portion of the plunger from moving perpendicular to a longitudinal axis of the syringe barrel.

7. The syringe as recited in claim 5, wherein the guide has a shape that is cooperative with a shape of an indentation formed within the external portion of the plunger so that the external portion of the plunger fits over at least a portion of the guide and slides along the guide in a longitudinal direction relative to the syringe barrel.

8. The syringe as recited in claim 7, wherein a cross-section of the guide is polygonal except for a curved side that conforms to a curvature of the syringe barrel, such that the curved side of the guide forms a continuous interface between the guide and an external surface of a cylindrical body of the syringe barrel.

9. The syringe as recited in claim 8, wherein the cross-section of the guide is pentagonal except for the curved side.

10. The syringe as recited in claim 1, wherein the syringe barrel has a first end with an opening for receiving the plunger and a second end with a second opening for receiving or dispensing the fluid, the first end of the syringe barrel also having a flange disposed about the opening, the flange including a notch that at least partially surrounds the external portion of the plunger.

11. A syringe plunger, comprising:
    a base;
    an internal portion having a first end coupled to the base, the internal portion configured to extend longitudinally into a syringe barrel and having a second end configured to push a fluid out of the syringe barrel; and
    an external portion having a first end coupled to the base, the external portion configured to extend longitudinally along an outer surface of the syringe barrel and having a projection disposed at a second end of the external portion, the projection configured to receive an applied force that causes an entirety of the plunger to move relative to the syringe barrel so that the second end of the internal portion is actuated through a portion of the syringe barrel, wherein a distance between the second end of the internal portion and the projection is less than a distance between the base and the projection, wherein the projection is perpendicular to the external portion of the plunger, wherein the projection extends a distance of 5 to 15 mm from the external portion of the plunger, wherein the projection includes surface texturing comprising a pattern of protuberances on the projection, and wherein the external portion of the plunger includes additional surface texturing on a surface of the external portion that is adjacent to the projection.

12. The syringe plunger as recited in claim 11, wherein the internal portion and the external portion are perpendicular to the base and parallel to one another.

13. The syringe plunger as recited in claim 11, wherein the base, the external portion, and the internal portion are formed from a common mold or print.

14. The syringe plunger as recited in claim 11, wherein the external portion includes an indentation configured to fit over at least a portion of a guide on the outer surface of the syringe barrel so that the external portion slides along the guide in a longitudinal direction relative to the syringe barrel.

15. The syringe plunger as recited in claim 14, wherein a cross-section of the indentation is polygonal.

16. The syringe plunger as recited in claim 15, wherein the cross-section of the indentation is pentagonal.

\* \* \* \* \*